US00PP32446P2

(12) United States Plant Patent
Hoogendoorn

(10) Patent No.: US PP32,446 P2
(45) Date of Patent: Nov. 10, 2020

(54) ***ZYGOPETALUM* ORCHID PLANT NAMED 'CAMHYLWIP'**

(50) Latin Name: *Zygopetalum*
Varietal Denomination: CAMHYLWIP

(71) Applicant: ANTHURA B.V., Bleiswijk (NL)

(72) Inventor: Gert-Jan Hoogendoorn, Woubrugge (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/873,253

(22) Filed: Mar. 5, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Zygopetalum* plant named 'CAMHYLWIP', particularly characterized by having dark purplish-red, flecked, fragrant flowers with large violet-white lips, leaves that are lanceolate and moderately elongated, and is propagated by meristem tissue culture, is disclosed.

3 Drawing Sheets

Genus and species: *Zygopetalum.*
Variety denomination: 'CAMHYLWIP'.

BACKGROUND OF THE NEW PLANT

The present invention relates to a new and distinct cultivar of *Zygopetalum* plant, botanically known as *Zygopetalum* of the Orchidaceae family, and hereinafter referred to by the cultivar name 'CAMHYLWIP'.

*Zygopetalum, Huntleya, Pabstia, Pescatorea, Promenaea, Warrea* and some other genera are a complex group of orchid species that are easily hybridized. The boundaries between the genera have been under discussion for the last several decades. *Zygopetalum* is a genus of the orchid family consisting of sixteen currently recognized species. All *Zygopetalum* plants exhibit a sympodial growth habit. The species have small ovoid-conical pseudobulbs, which are extensions of the rhizome. They typically have 3 to 6 leaves per pseudobulb. The leaves are plicate at the base, widening and lying flat apically, minimally narrowed basally to contract with the duplicate petioles and arranged in the form of an open fan. The peduncles vary in size from 20.0 cm to 60.0 cm.

*Zygopetalum* orchids are used as flowering potted plants for the home or interiorscape. *Zygopetalum* produce upright or pendent lateral raceme inflorescences that hold the star-shaped, waxy-texture flowers, some of which are fragrant. The flowers possess three sepals, two petals, and a lip, which is rather fleshy and one- to three-lobed. The lateral lobes of the lip are small and almost invisible. The hypochil of the lip has a basal callus with an erect, U- of V-shaped, fimbriate margin. Flower colors include various shades of green, purple, green-brown, white, and yellow. *Zygopetalum* orchids are typically propagated from tissue culture. Asexual propagation of *Zygopetalum* is often done from off-shoots which arise from the lower bracts of the inflorescence. The resulting plants are detached from the mother plants and may be planted in a suitable substrate.

The new *Zygopetalum* 'CAMHYLWIP' is particularly characterized by its attractive and unique dark purplish-red, flecked flowers with large violet-white lips, economical propagation by tissue culture, early flowering, and a plant dimension suitable for packaging and shipping to the market.

The new *Zygopetalum* plant 'CAMHYLWIP' is the product of a planned breeding program conducted by the inventor in Bleiswijk, the Netherlands. 'CAMHYLWIP' originated from a cross made by the inventor in November 2008 in Bleiswijk, the Netherlands. The female parent was a green-purple *Zygopetalum* pot plant named '75000-0111' (unpatented) and the male parent was a green-brown *Zygopetalum* pot plant named '75000-063' (unpatented). The new *Zygopetalum* was selected by the inventor as a single plant within the progeny of the stated cross-pollination in a controlled greenhouse in Bleiswijk, the Netherlands, in June 2011.

Asexual reproduction of 'CAMHYLWIP' by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 20, 2018, by Applicant who obtained the subject matter disclosed directly from the inventor. 'CAMHYLWIP' has not been made publicly available or sold anywhere in the world prior to the effective filing date of this application with the exception of sales or disclosures made one year or less before the effective filing date of this claimed invention by Applicant who obtained 'CAMHYLWIP' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'CAMHYLWIP' as a new and distinct variety of *Zygopetalum* plant:

1) Dark purplish-red, flecked flowers with large violet-white lips;
2) Fragrant flowers; and
3) Lanceolate and moderately elongated leaf shape.

DESCRIPTION OF THE PHOTOGRAPHS

This new *Zygopetalum* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 60-week-old plants in January 2020. Colors in the photographs may differ from the color values cited in the detailed botanical description, which accurately describe the actual colors of the new variety.

DESCRIPTION OF THE NEW VARIETY

Figure 1:
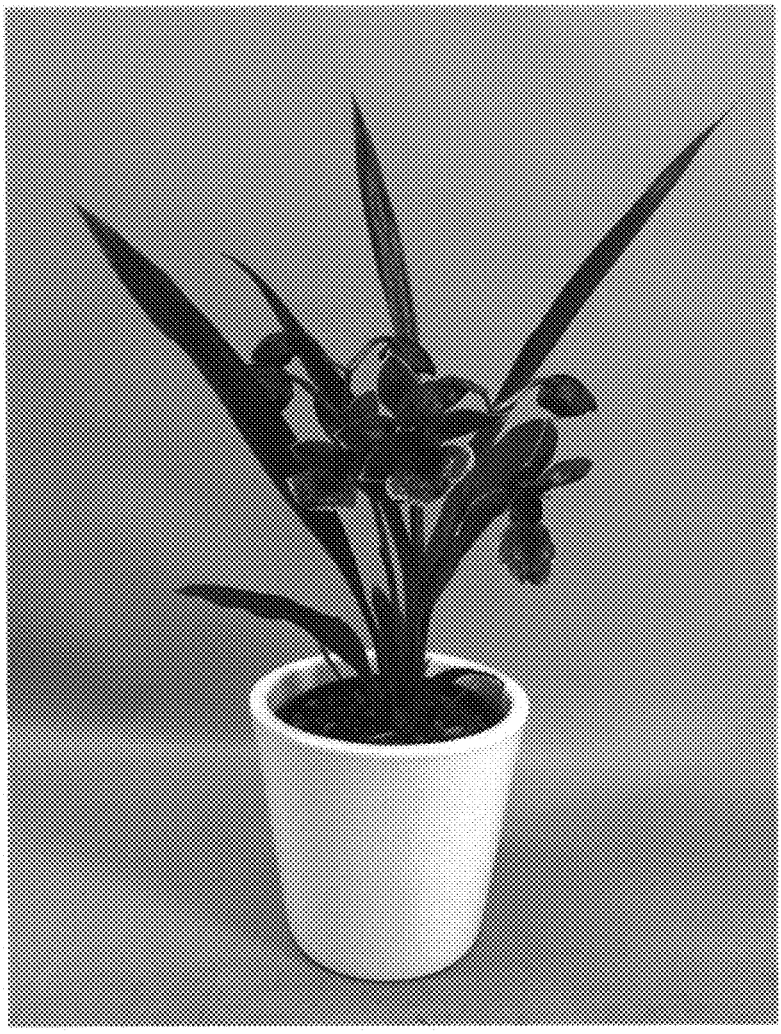
FIG. 1 shows the overall plant habit, including blooms, buds, and foliage of 'CAMHYLWIP'.
Figure 2:
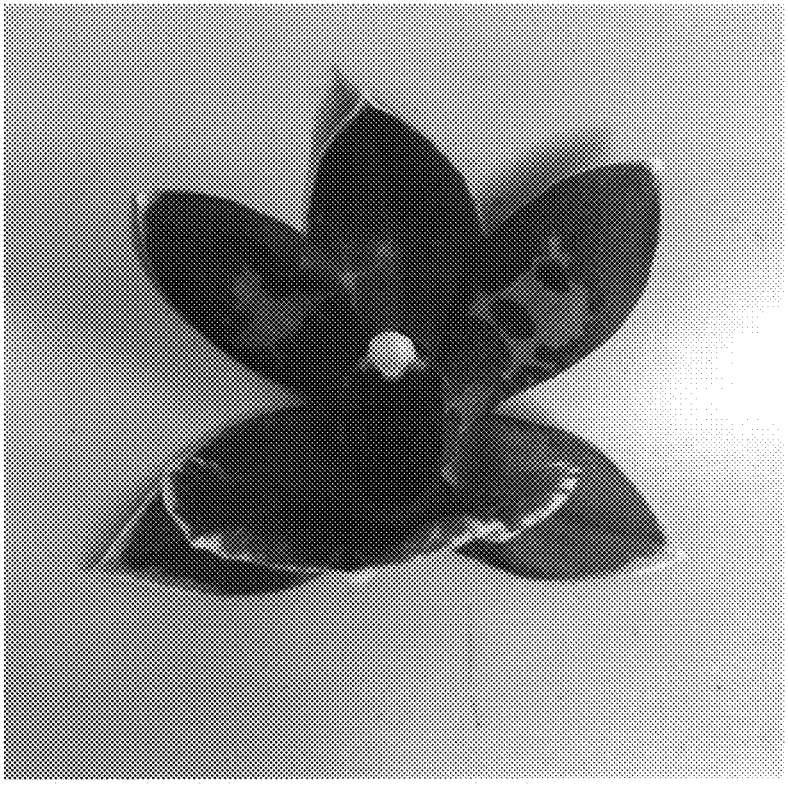
FIG. 2 shows a close-up of a flower of 'CAMHYLWIP'.
Figure 3:
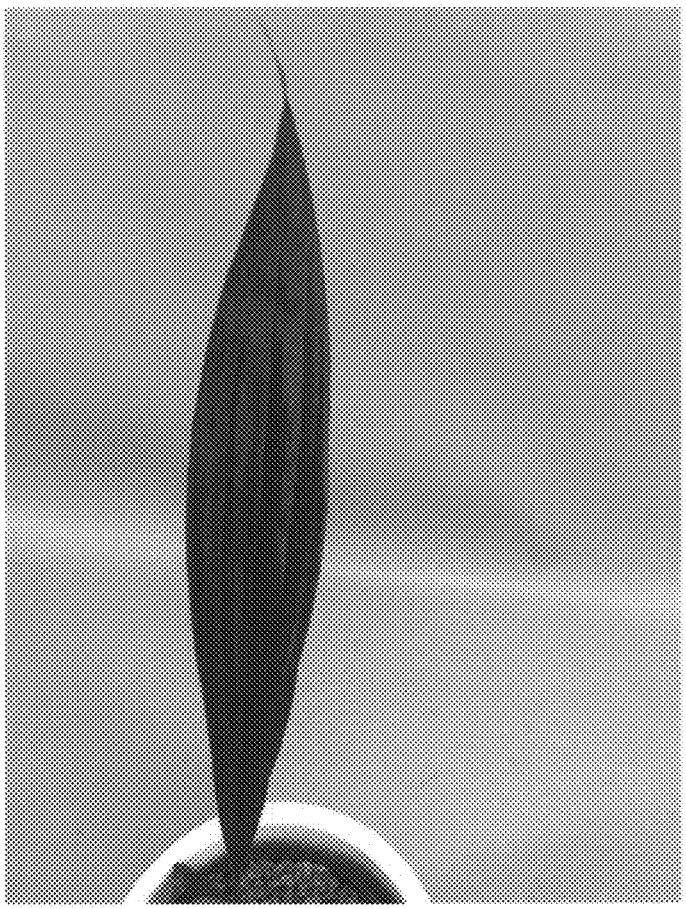
FIG. 3 shows an overhead view of the leaves of 'CAMHYLWIP'.

The following detailed description sets forth the distinctive characteristics of 'CAMHYLWIP'. The data which define these characteristics were collected from asexual reproductions carried out in Bleiswijk, the Netherlands. Observations and measurements were made in January 2020 on 60-week-old plants which were planted from tissue culture in 12-centimeter (diameter) pots and grown in a greenhouse between 21° C. to 27° C. for 40 weeks. The temperature between day and night time could be +/−10° C. Color readings were taken under 4000-6000 lux natural light in a greenhouse in Bleiswijk, the Netherlands. Color references are primarily to The R.H.S. Colour Chart of The Royal Horticultural Society, London, England, 2015 edition, except where general color terms of ordinary significance are used.

DETAILED BOTANICAL DESCRIPTION

Classification:
- *Family.*—Orchidaceae.
- *Botanical.*—*Zygopetalum.*
- *Common name.*—*Zygopetalum.*
- *Variety name.*—'CAMHYLWIP'.

Parentage:
- *Female parent.*—*Zygopetalum* cultivar '75000-0111' (unpatented).
- *Male parent.*—*Zygopetalum* cultivar '75000-063' (unpatented).

Propagation:
- *Type.*—Meristem tissue culture.

Plant:
- *Crop time (time to produce a finished flowering plant).*—60 to 80 weeks in a 12-cm pot.
- *Growth habit of the peduncle.*—Standard, green leaves, raceme.
- *Height (measured from soil, including inflorescence).*—25.0 cm to 35.0 cm.
- *Width (measured from leaf tips).*—27.0 cm to 32.0 cm.
- *Vigor.*—Moderate.

Roots:
- *Root description.*—White (RHS 155B) colored roots with light greenish-yellow (RHS 4A) growing tips (the exact shade of white may vary with minimal changes of environmental conditions).

Pseudobulb:
- *Number of pseudobulbs.*—1 to 2.
- *Shape.*—Laterally compressed ovoid.
- *Length.*—2.5 cm to 3.5 cm.
- *Width.*—1.0 cm to 1.5 cm.
- *Thickness.*—0.8 cm to 0.9 cm.
- *Color.*—Green (RHS 146A).

Leaves:
- *Mature leaves.*—Quantity per pseudobulb: 3 to 6 leaves are produced before flowering. Length (fully expanded): 27.0 cm to 32.0 cm. Width: 3.5 cm to 4.5 cm. Shape: Lanceolate. Base shape: Moderately elongated. Apex: Acute. Leaf margin: Entire. Color: Upper surface: RHS 146A. Lower surface: RHS 146B. Texture (both upper and lower surfaces): Smooth. Thickness: 0.3 mm to 0.4 mm. Venation: Pattern: Parallel. Color of the midvein: Upper surface: RHS 146A. Lower surface: RHS 146B.

Peduncle:
- *Quantity per plant.*—1 to 2.
- *Number of flowers per peduncle.*—4 to 6.
- *Length.*—From 25.0 cm to 35.0 cm.
- *Diameter.*—4.0 mm to 5.0 mm.
- *Strength.*—Moderate.
- *Aspect.*—Upright.
- *Texture.*—Smooth.
- *Color.*—Green (RHS 146C).
- *Internode length.*—65.0 mm to 70.0 mm.
- *Number of branches.*—0.

Inflorescence description:
- *Appearance.*—Upright, raceme inflorescence with bilaterally symmetrical flowers that open in succession beginning with the lowermost flower.
- *Inflorescence size.*—Height (from base to tip): 100.0 mm to 120.0 mm.
- *Flowering time.*—First flowers can be expected 4 to 6 months after planting in a 12-cm pot.
- *Flower.*—Height: 58.0 mm to 63.0 mm. Diameter: 65.0 mm to 70.0 mm.
- *Flower longevity.*—On the plant: 3 to 5 weeks.
- *Fragrance.*—Present (degree of fragrance is moderate).
- *Flower bud.*—Length: 26.0 mm to 28.0 mm. Width: 15.0 mm to 17.0 mm. Color: Yellowish-brown (RHS 200A to 200B).
- *Petals.*—Shape: Elliptic. Apex: Obtuse. Margin: Even. Length (from base to tip): 31.0 mm to 33.0 mm. Width: 16.0 mm to 18.0 mm. Color (when fully opened): Upper surface: Basic color: Dark purplish-red (RHS N79B). Over color: Yellow-green flecks (RHS 195B) and light yellow-green tips (RHS 196B). Lower surface: Basic color: Mix of dark purplish-red (RHS N79B) and reddish-purple (RHS N77C). Over color: Light yellow-green margin (RHS 196C) toward the tip.
- *Dorsal sepal.*—Shape: Elliptic. Apex: Acute. Margin: Even. Length (from base to tip): 37.0 mm to 39.0 mm. Width: 18.0 mm to 20.0 mm. Color (when fully opened): Upper surface: Basic color: Dark purplish-red (RHS N79B). Over color: Slightly light yellow-green (RHS 145B) at the base; yellow-green flecks (RHS 195B) and light yellow-green margin (RHS 196A) toward the tip. Lower surface: Basic color: Mix of dark purplish-red (RHS N79B) and reddish-purple (RHS N77C). Over color: Yellow-green stripe (RHS 145A) at the base; light yellow-green margin (RHS 196B) toward the tip.

*Lateral sepals*.—Shape: Elliptic. Apex: Acute. Margin: Entire. Length (from base to tip): 34.0 mm to 36.0 mm. Width: 18.0 mm to 20.0 mm. Color (when fully opened): Upper surface: Basic color: Dark purplish-red (RHS N79B). Over color: Few flecks (RHS 195B); light yellow-green margin (RHS 196A) toward the tip. Lower surface: Basic color: Mix of dark purplish-red (RHS N79B) and reddish-purple (RHS N77C). Over color: Touch of yellow-green (RHS 195B); light yellow-green margin (RHS 196B) toward the tip.

*Labellum* (*lip*).—Lateral lobe: Length: 8.0 mm to 10.0 mm. Width: 5.0 mm to 7.0 mm. Color: Upper surface: Violet (RHS 86A to 86B) and white (RHS N155A) at the margin. Lower surface: Very light purple (RHS 85D) with purple flecks (RHS 83B). Margin: Slightly undulated. Apical lobe: Shape: Heart-shaped at the base. Margin: Undulated. Length: 24.0 mm to 26.0 mm. Width: 38.0 mm to 40.0 mm. Color: Upper surface: Violet (RHS 86A to 86B) and white (RHS N155A) toward the margin. Lower surface: Very light purple (RHS 85C to 85D) with purple flecks (RHS 83B). Callus: Shape: U-shaped. Height: 7.0 mm to 9.0 mm. Width (in front view): 12.0 mm to 14.0 mm. Color: Purple (RHS 83A).

Reproductive organs:

*Arrangement*.—The stamens, style, and stigmas are fused into a single, short structure called the column, possessing one terminal anther with pollen grains united into pollinia, which are covered by an anther cap. The stigma is located under the column behind the pollinia. The ovary is inferior with three carpels present. Column: Length: 11.0 mm to 13.0 mm. Diameter: 8.0 mm to 9.0 mm. Color: Dark purple (RHS 83A). Wings: Absent. Cap: Average size: 3.0 mm to 4.0 mm. Shape: Oval cup. Color: White (RHS 158C to 158D). Pollinia: Quantity: 2. Diameter: 0.4 mm to 0.6 mm. Color: Yellow (RHS 12A). Ovary: Length: 8.0 mm to 10.0 mm. Diameter: 2.9 mm to 3.2 mm. Pedicel: Length: 29.0 mm to 32.0 mm. Diameter: 2.6 mm to 2.8 mm. Color: Yellow-green (RHS 144B).

Disease, pest, and stress resistance: No specific resistance or susceptibility observed to date.

Temperature tolerance: Not observed to date.

COMPARISON WITH PARENTAL LINES AND MOST SIMILAR VARIETIES

'CAMHYLWIP' differs from female parent plant '75000-0111' (unpatented) in that 'CAMHYLWIP' has dark purplish-red flowers and a straight curvature of the dorsal sepal longitudinal axis, whereas '75000-0111' has creamy blue flowers and an incurving curvature of the dorsal sepal longitudinal axis.

The male parent plant of 'CAMHYLWIP', cultivar '75000-063' (unpatented), is no longer in existence, therefore a meaningful comparison cannot be made.

'CAMHYLWIP' is most similar to the commercial *Zygopetalum* plants named 'CAMHALWEM' (unpatented) and 'CAMHOLXYM' (unpatented). 'CAMHYLWIP' differs from the commercial variety 'CAMHALWEM' in that 'CAMHYLWIP' has acute dorsal sepal apexes and yellowish-brown flower buds, whereas 'CAMHALWEM' has obtuse dorsal sepal apexes and green flower buds.

'CAMHYLWIP' differs from the commercial variety 'CAMHOLXYM' in that 'CAMHYLWIP' has dark purplish-red flowers and yellowish-brown flower buds, whereas 'CAMHOLXYM' has green flowers and green flower buds. Additionally, 'CAMHYLWIP' has wider dorsal sepals than 'CAMHOLXYM'.

I claim:

1. A new and distinct variety of *Zygopetalum* plant named 'CAMHYLWIP', substantially as described and illustrated herein.

* * * * *